(12) United States Patent
Rogers et al.

(10) Patent No.: US 10,371,628 B2
(45) Date of Patent: Aug. 6, 2019

(54) APPARATUS FOR MEASURING SPECTRAL HEMISPHERICAL REFLECTANCE OF SAMPLES AT GRAZING ANGLES

(71) Applicant: The Boeing Company, Chicago, IL (US)

(72) Inventors: Mark D. Rogers, Ballwin, MO (US); Loyal Bruce Shawgo, O'Fallon, MO (US); Jeffery Thomas Murphy, Troy, MO (US)

(73) Assignee: The Boeing Company, Chicago, IL (US)

( * ) Notice: Subject to any disclaimer, the term of this patent is extended or adjusted under 35 U.S.C. 154(b) by 8 days.

(21) Appl. No.: 15/670,550

(22) Filed: Aug. 7, 2017

(65) Prior Publication Data

US 2019/0041323 A1   Feb. 7, 2019

(51) Int. Cl.
| | | |
|---|---|---|
| *G01J 3/50* | (2006.01) | |
| *G01J 3/51* | (2006.01) | |
| *G01N 21/47* | (2006.01) | |
| *G01N 21/85* | (2006.01) | |
| *G01N 21/359* | (2014.01) | |
| *G01N 21/3563* | (2014.01) | |

(52) U.S. Cl.
CPC ............ *G01N 21/359* (2013.01); *G01J 3/506* (2013.01); *G01J 3/513* (2013.01); *G01N 21/3563* (2013.01); *G01N 21/474* (2013.01); *G01N 21/85* (2013.01)

(58) Field of Classification Search
CPC ........ G01J 3/506; G01J 3/513; G01J 21/3563; G01J 21/474; G01J 21/85
See application file for complete search history.

(56) References Cited

U.S. PATENT DOCUMENTS

| | | | | |
|---|---|---|---|---|
| 4,921,351 | A | * 5/1990 | Kohigashi | ................. G01J 3/42 250/228 |
| 4,991,106 | A | * 2/1991 | Judge | .................. G01R 31/308 324/102 |
| 5,475,234 | A | * 12/1995 | Xu | ..................... A61B 5/14532 250/573 |

(Continued)

OTHER PUBLICATIONS

Erik Torgerson et al; DHR Measurements Technical Report; Jun. 20, 2017.

(Continued)

*Primary Examiner* — Dominic J Bologna
(74) *Attorney, Agent, or Firm* — Duft & Bornsen, PC (57) ABSTRACT

Systems and methods are provided for measuring spectral hemispherical reflectance. One embodiment is a system that includes a laser that emits a beam of light, and an optical chopper disposed between the laser and a sample. The chopper blocks the beam while the chopper is at a first angle of rotation, redirects the beam along a reference path while the chopper is at a second angle of rotation, and permits the beam to follow a sample path through the chopper and strike the sample while the chopper is at a third angle of rotation. The system also includes a hollow sphere that defines a slot through which the sample path and reference path enter the sphere. The hollow sphere includes a spectral hemispherical reflectance detector, a mount that receives the sample at the sphere, and an actuator that rotates the sphere about an axis that intersects the sample.

20 Claims, 7 Drawing Sheets

(56) References Cited

U.S. PATENT DOCUMENTS

2002/0183600 A1* 12/2002 Tsenkova ............... G01N 21/31
                                                        600/310
2002/0198441 A1* 12/2002 Tsenkova ............. G01N 21/359
                                                        600/310

OTHER PUBLICATIONS

Integrating Sphere Theory and Applications.
Robert A. Shepherd; Proceedings Article; Absolute measurement of diffuse and specular reflectance using an FTIR spectrometer with an integrating sphere; Sep. 1, 1990.
Shannon L. Storm; The Use of Center Mount Sample Holders in Reflectance Spectroscopy; Jan. 1998 Application Note No. 02.
SOC-100 HDR Hemispherical Directional Reflectometer; Surface Optics Corporation.

* cited by examiner

APPARATUS FOR MEASURING SPECTRAL HEMISPHERICAL REFLECTANCE OF SAMPLES AT GRAZING ANGLES

FIELD

The disclosure relates to the field of optics, and in particular, to devices that measure reflectance of materials.

BACKGROUND

Measuring the spectral directional hemispherical reflectance of a sample remains a complex task. Such a process may involve placing a reference material having a known level of reflectance in a measuring device, measuring reflectance values of the reference material, removing the reference material from the device, determining a correction value based on the measured values for the reference material, replacing the reference material with a sample to be measured, and then finally measuring the sample.

These issues are compounded when attempting to accurately measure reflectance of a sample at high angles of incidence (i.e., angles that are close to tangential/parallel with the surface) at a high degree of accuracy. Some devices attempt to account for this issue by utilizing an interior surface of the measuring device as a reference material. However, such devices are capable of only single angle measurements, which substantially increases the amount of labor involved in quantifying the reflectance of a sample at a variety of angles of incidence.

Because of the issues described above, designers of devices that measure spectral hemispherical reflectance continue to seek out enhanced designs that are capable of rapidly measuring reflectance across a variety of angles of incidence, and that also are capable of accounting for potential sources of error when taking such measurements.

Therefore, it would be desirable to have a method and apparatus that take into account at least some of the issues discussed above, as well as other possible issues.

SUMMARY

Embodiments described herein provide systems which are capable of engaging in measurement of spectral hemispherical reflectance of a sample across a wide range of angles, and without the need for replacing a sample with a reference material. Specifically, the systems described herein engage in Time Domain Multiplexing (TDM) of a laser in order to quickly acquire a zero signal, reference signal, and sample signal for each angle of incidence at the sample. The reference signal measures hemispherical reflectance at an inner surface of a sphere in which the sample is disposed. TDM may be accomplished via an optical chopper which physically redirects the laser, blocks the laser, or allows the laser to pass through to the sample.

One embodiment is a system that includes a laser that emits a beam of light, and an optical chopper disposed between the laser and a sample. The chopper blocks the beam while the chopper is at a first angle of rotation, redirects the beam along a reference path while the chopper is at a second angle of rotation, and permits the beam to follow a sample path through the chopper and strike the sample while the chopper is at a third angle of rotation. The system also includes a hollow sphere that defines a slot through which the sample path and reference path enter the sphere. The hollow sphere includes a spectral hemispherical reflectance detector, a mount that receives the sample at the sphere, and an actuator that rotates the sphere about an axis of rotation that intersects the sample.

A further embodiment is a method that includes emitting a beam of light from a laser, and time domain multiplexing the beam. This causes the beam to iteratively follow a sample path that proceeds through a slot at a hollow sphere to strike a sample at the sphere, follow a reference path that proceeds through the slot to strike an interior surface of the sphere, and be blocked. The method also includes acquiring, via a detector within the sphere, measurements of spectral hemispherical reflectance while the beam is being time domain multiplexed, and correlating the measurements with time periods when the beam followed the sample path, followed the reference path, and was blocked. The method additionally involves calculating a spectral hemispherical reflectance of the sample based on the correlated measurements, and updating a memory with the calculated spectral hemispherical reflectance of the sample.

A further embodiment is a non-transitory computer readable medium embodying programmed instructions which, when executed by a processor, are operable for performing a method. The method includes emitting a beam of light from a laser, and time domain multiplexing the beam. This causes the beam to iteratively follow a sample path that proceeds through a slot at a hollow sphere to strike a sample at the sphere, follow a reference path that proceeds through the slot to strike an interior surface of the sphere, and be blocked. The method also includes acquiring, via a detector within the sphere, measurements of spectral hemispherical reflectance while the beam is being time domain multiplexed, and correlating the measurements with time periods when the beam followed the sample path, followed the reference path, and was blocked. The method additionally involves calculating a spectral hemispherical reflectance of the sample based on the correlated measurements, and updating a memory with the calculated spectral hemispherical reflectance of the sample.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
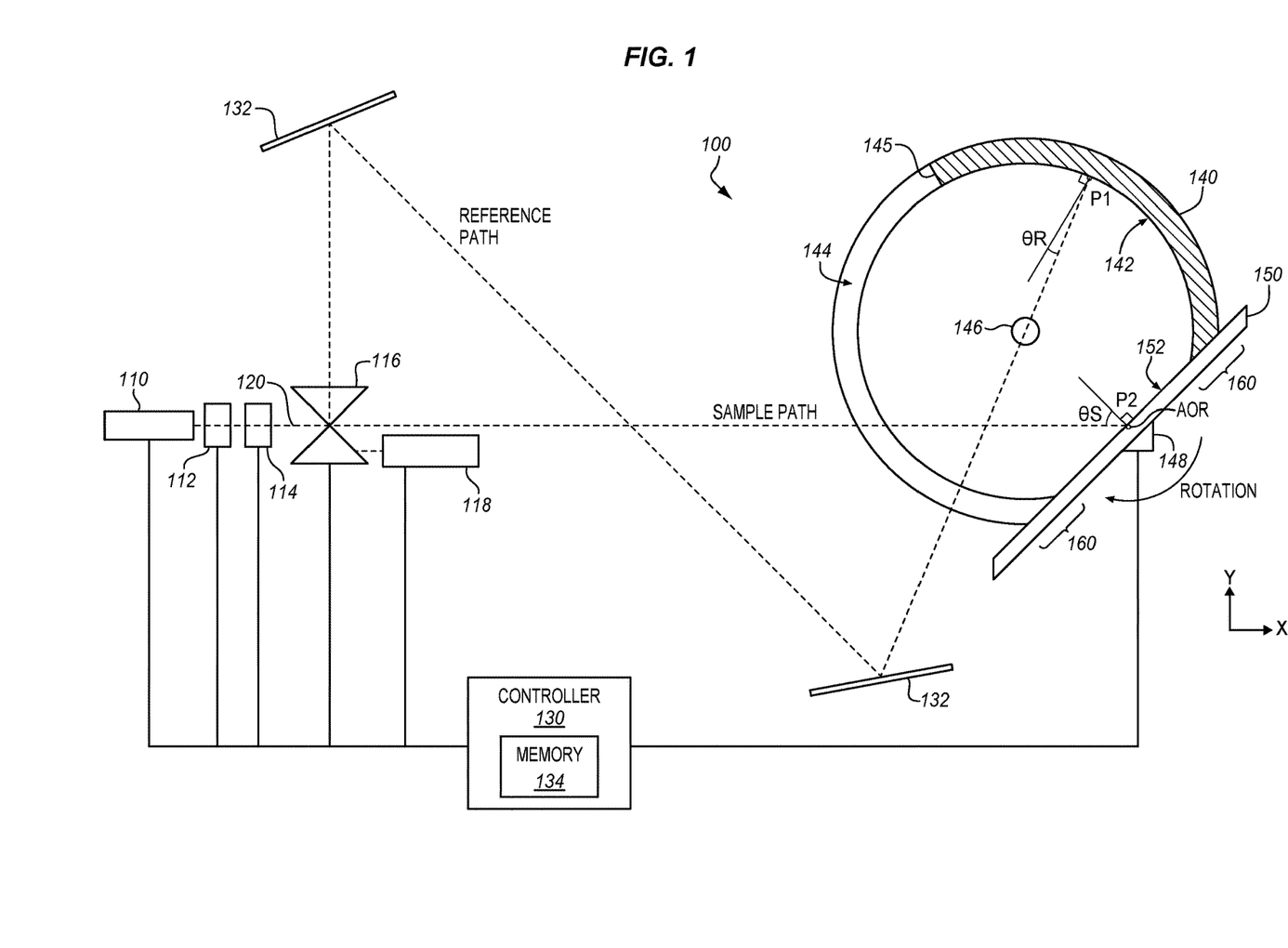
FIG. 1 is a top cut-through view of a system for measuring spectral hemispherical reflectance of a sample in an exemplary embodiment.
Figure 2:
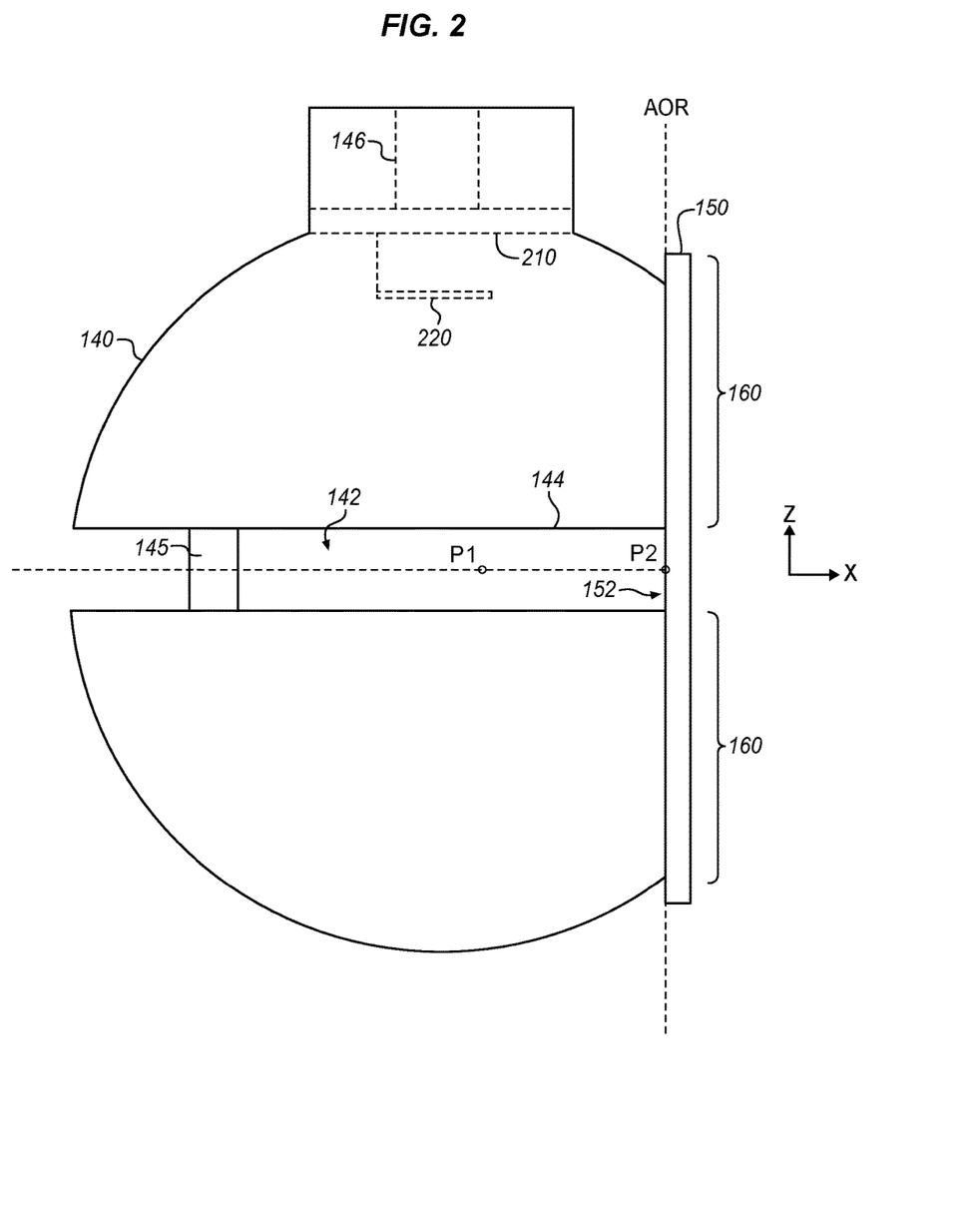
FIG. 2 is a side view of a sphere utilized in the system of FIG. 1 in an exemplary embodiment.

FIGS. 1-2 illustrate views of a system for measuring spectral hemispherical reflectance of a sample in an exemplary embodiment. This system may be utilized to measure spectral hemispherical reflectance of a sample at high angles of incidence (e.g., eighty degrees or more, such as eighty seven degrees or more). As used herein, such angles are referred to as "grazing angles" because the laser beam "grazes" the sample at these high angles of incidence.

FIG. 1 is a top cut-through view of spectral hemispherical measurement system 100 in an exemplary embodiment. System 100 comprises any combination of components or devices that are capable of measuring spectral hemispherical reflectance at a surface 152 of a sample 150 across multiple angles of incidence. In this embodiment, system 100 includes laser 110 (e.g., a wavelength-tunable laser), which generates a beam of laser light that travels through half-wave plate 112 and polarizer 114, which linearly polarize the beam prior to the beam reaching location 120. In further embodiments, laser 110 may be steered by a beam-steering instrument and/or shaped by a concave mirror as desired.

The polarized beam proceeds through optical chopper 116 (e.g., a rotatable wheel), which physically engages in TDM of the beam. That is, the beam is iteratively sent along a sample path to sample 150, redirected across reflective elements 132 (e.g., mirrors) along a reference path, and blocked. As used herein, while the beam is sent along the sample path it is referred to as being in the sample state, while the beam is sent along the reference path it is referred to as being in the reference state, and while the beam is blocked it is referred to as being in the blocked state. In some embodiments, the reference path intersects the sample path at between thirty and sixty degrees (e.g., forty-five degrees) within sphere 140. This may result, for example, from features of the design which allow the beam to pass into sphere 140 through the slot across a wide range of angles along both the reference path and sample path.

Chopper 116 rotates such that the beam repeatedly transitions through the three states, such that the states repeat a rate of 60-100 Hertz (Hz). A surface of chopper 116 may be machined to a predefined degree of smoothness (e.g., sub-micron flatness) in order to minimize wobble of beams in the reference state at an inner surface of sphere 140. Sensor 118 measures the rotation of chopper 116, and provides signaling to controller 130 enabling controller 130 to correlate different time periods with the different states of laser 110 (e.g., sample state, reference state, zero state). Controller 130 may be implemented, for example, as custom circuitry, as a hardware processor executing programmed instructions, or some combination thereof.

Beams of light from laser 110 continuing along the reference path travel through arcuate slot 144, striking point P1 of inner surface 142 of hollow sphere 140 at an angle of incidence θR. Inner surface 142 may be made from a diffuse reflective material having known reflectance properties. Inner surface 142 may be a spherical surface that, while machined accurately, has a relatively rough diffuse reflective surface.

Beams of light from laser 110 traveling through the sample path also travel through slot 144, but strike point P2 at surface 152 of sample 150 at an angle of incidence θS. At high angles of incidence, the footprint of the beam at surface 142 increases. Slot 144 terminates at wall 145, and sample 150 is held to sphere 140 at mounts 160. In one embodiment, sample 150 is held in place at mounts 160 by a vacuum chuck (not shown), and is pressed against mounts 160.

Spectral hemispherical reflectance detector 146 measures reflectance to acquire zero, reference, and sample values for spectral hemispherical reflectance. Detector 146 may comprise any suitable light detector. In one embodiment, detector 146 comprises a Mercury Cadmium Telluride (MCT) detector that detects long-wave Infrared (IR) light, although other types of detectors may be utilized to detect light having different wavelengths (e.g., mid-range IR, visible light, ultraviolet (UV) light, etc.).

Controller 130 receives input from detector 146, which is used to calculate a spectral hemispherical reflectance of sample 150. This input may be pre-amplified, filtered with a low-pass filter, Analog-to-Digital (A/D) converted, and stored in memory 134 such that each input measurement is associated with a different point in time.

Controller 130 may further correlate the input with zero states, reference states, and/or sample states based on timing input from sensor 118. After one or more sample, reference, and zero measurements have been acquired as input for a given angle of incidence, controller 130 may direct actuator 148 to rotate sphere 140 about an off-center Axis of Rotation (AOR) that intersects P2 in order to change the angle of incidence for a next set of measurements. In this manner, system 100 may rapidly acquire zero input, sample input, and reference input at a variety of angles of incidence, including high angles of incidence such as eighty seven degrees and even higher (the range of angles measured may include angles between zero degrees and eighty seven degrees). Furthermore, this measurement process is performed without the need to replace sample 150 with a reference material, since inner surface 142 of sphere 140 is utilized for this purpose. Such practices beneficially eliminate substitution errors that are common when engaging in spectrophotometry.

FIG. 2 is a side view of sphere 140 of FIG. 1 in an exemplary embodiment. FIG. 2 illustrates similar features to those of FIG. 1, but also further illustrates a mount 210 that detector 146 is attached to. FIG. 2 also illustrated a baffle 220 that is vertically interposed (i.e., along Z) between detector 146 and the sample path and reference path. Baffle 220 prevents detector 146 from receiving first bounce reflection from P1 and P2. Baffle 220 may be made of a diffusive reflective material. In this embodiment, detector 146 includes an internal baffle (not shown) that limits its detection radius to a sixty degree cone. Thus, because baffle 220 is interposed between detector 146 and the inner surface 142 of sphere 140, the sixty degree cone of vision of detector 146 is blocked from directly viewing the inner surface 142 of sphere 140.

Illustrative details of the operation of system 100 will be discussed with regard to FIG. 3. Assume, for this embodiment, that sample 150 has been mounted to sphere 140, and that sample 150 awaits testing to determine its spectral hemispherical reflectance at a variety of angles of incidence (including high angles of incidence such as eighty seven degrees and higher), wavelengths, and/or polarizations.

Figure 3:
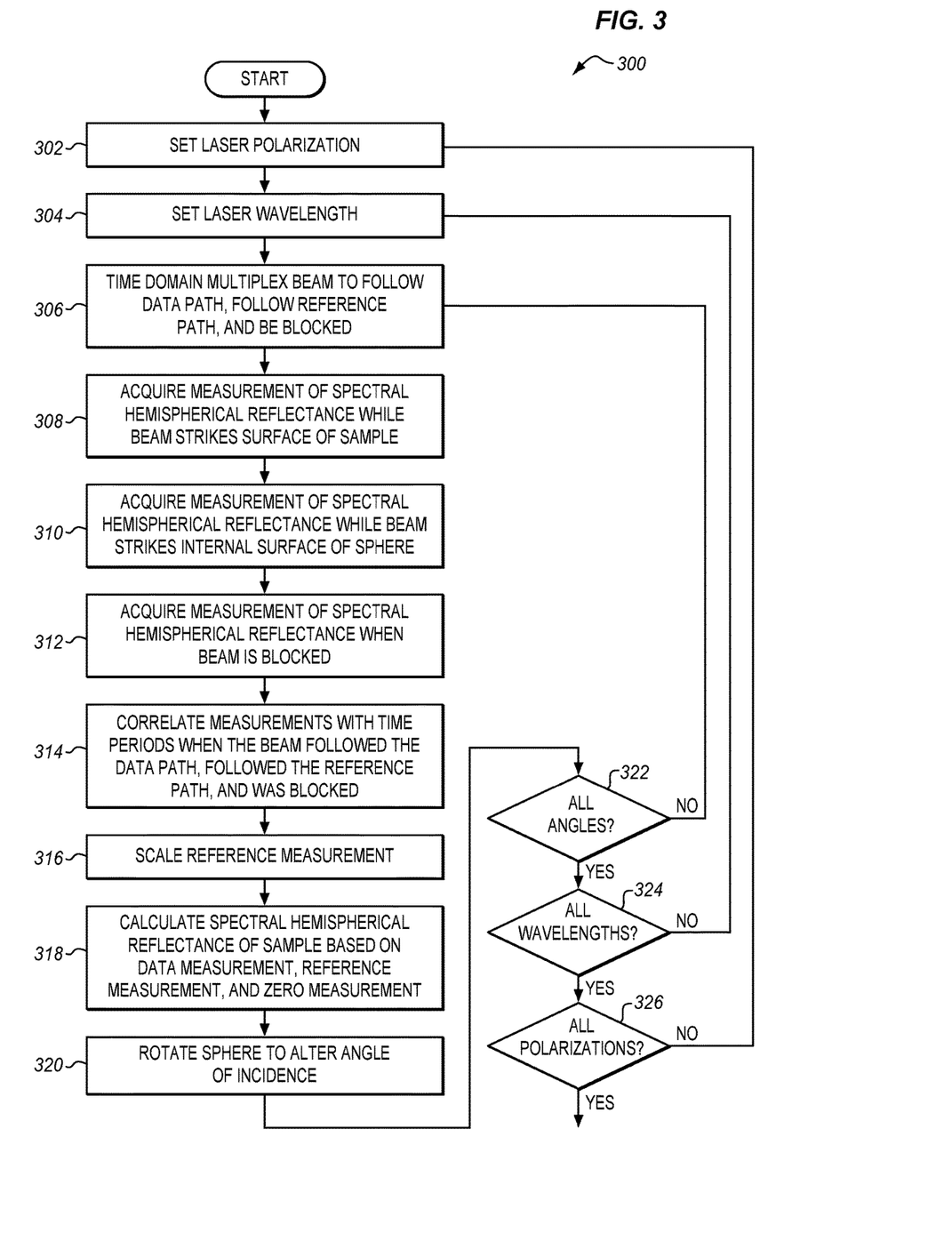
FIG. 3 is a flowchart illustrating a method for operating a system that measures spectral hemispherical reflectance at a variety of angles, wavelengths, and/or polarizations in an exemplary embodiment.

FIG. 3 is a flowchart illustrating a method 300 for operating a system that measures spectral hemispherical reflectance of a sample at a variety of angles, wavelengths, and/or polarizations in an exemplary embodiment. The steps of method 300 are described with reference to system 100 of FIG. 1, but those skilled in the art will appreciate that method 300 may be performed in other systems. The steps of the flowcharts described herein are not all inclusive and may include other steps not shown. The steps described herein may also be performed in an alternative order.

Laser polarization is set by rotating half-wave plate 112 and polarizer 114. These components will cause a beam from laser 110 to become linearly polarized along a desired direction (step 302). Laser 110 is tuned to a desired wavelength (step 304). Laser 110 is further activated to emit a beam of light, and chopper 116 initiates rotating. As chopper 116 rotates, it Time Domain Multiplexes the beam to iteratively follow the sample path, follow the reference path, and be blocked (step 306). While a chopper is utilized to perform TDM of the beam in this example, in further embodiments other systems, components, or devices may be utilized.

As the beam is iteratively cycled between the zero state, reference state, and sample state, controller 130 operates detector 146 to acquire input comprising measurements of spectral hemispherical reflectance. These measurements include measurements for the sample state acquired while the beam strikes surface 152 of sample, 150 (step 308), measurements for the reference state acquired while the beam strikes inner surface 142 of sphere 140 (step 310), and measurements for the zero state acquired while the beam is blocked (step 312). Because of the speed at which chopper 116 is engaging in TDM of the beam, controller 130 may acquire input across a large number of zero states, sample states, and reference states. For example, in one embodiment where chopper 116 cycles through the states at 100 Hz, controller 130 may acquire data corresponding with twenty five iterations of each state by acquiring measurements over one quarter of a second.

With the input measurements acquired, controller 130 may further analyze and unify these measurements in order to determine the spectral hemispherical reflectance of sample 150 for the current angle of incidence. To this end, controller 130 utilizes input from sensor 118 to determine which measurements correspond with sample states, which measurements correspond with reference states, and which measurements correspond with zero states. That is, controller 130 correlates the measurements with time periods when the beam followed the sample path, followed the reference path, and was blocked (step 314). Controller 130 may further determine which iteration of a state each measurement corresponds with, based on the input from sensor 118. For example, measurements acquired during the fifth iteration of the sample state may be grouped together, measurements acquired during the fifth iteration of the zero state may be grouped together, and so on.

In this embodiment, controller 130 also scales each reference measurement based on known reflectance properties of inner surface 142 (step 316). This ensures that reflectance data for the reference state is properly scaled before it is used to calculate the reflectance of sample 150.

For each iteration of a state, controller 130 averages the input measurements to determine an average value for that iteration of the state. In such an embodiment, the average value over a time period may be calculated according to the formula below, wherein N is the number of measurements reported by detector 146 during the time period correlated with an iteration of the state, i refers to the ith iteration of the sample state, and $D_m$ corresponds with an amount reported by detector 146 at a specific point in time for the ith iteration of the sample state. In embodiments where detector 146 samples at 10 KHz and chopper engages in TDM at 100 Hz, each iteration of a sample state may comprise approximately 33 data points/measurements.

$$VALUE_i = \frac{\sum_{m=1}^{n} D_m}{n} \quad (1)$$

In this manner, an average zero value, average sample value, and average reference value are calculated for each iteration as per equation (1) above. Controller 130 calculates spectral hemispherical reflectance of sample 150 based on the average sample value, average reference value, and average zero value (step 318). A reflectance value for each iteration may be calculated according to equation (2) below, wherein CF is a correction factor for the angle of incidence, AOI is an angle of incidence, and $\lambda$ is a wavelength:

$$REFLECTANCE_i = CF(AOI, \lambda)\frac{DATA_i - ZERO_i}{REFERENCE_i - ZERO_i} \quad (2)$$

The spectral hemispherical reflectance of sample 150 may then be calculated by averaging (e.g., calculating a mean, or selecting a median) the spectral hemispherical reflectance found in equation 2 across all iterations. This averaged value is the calculated spectral hemispherical reflectance of sample 150 at the angle of incidence.

With a reflectance value determined for sample 150 at the angle of incidence, controller 130 directs actuator 148 to alter the angle of incidence (step 320). If not all desired angles have already been measured (step 322), controller 130 returns to step 306. Else, controller 130 determines whether all desired wavelengths have already been measured (step 324). If not all desired wavelengths have been measured, controller 130 returns to step 304. Else, controller 130 determines whether all desired polarizations have been measured (step 326). If not controller 130 returns to step 302. Else, controller 130 continues, for example by storing the calculated reflectance values for sample 150 in memory 134.

Utilizing method 300 provides a substantial benefit because it enables reflectance of a sample to be accurately calculated without substitution error, without errors from laser drift, and with a tunable direction of polarization. That is, no error results from substitution, because sample 150 does not have to be replaced with a reference material. Furthermore, even though the power of laser 110 may drift over time, this will not cause substantial error because system 100 cycles through the sample state, zero state, and reference state multiple times per second. This means that, for each iteration, the states will be subject to the same amount of drift and hence error related to drift is eliminated. Method 300 also allows spectral hemispherical reflectance values for a large range of angles of incidence to be calculated quickly as part of an automated process. Thus, method 300 saves substantial amounts of time and labor in comparison with prior techniques.

Figure 4:
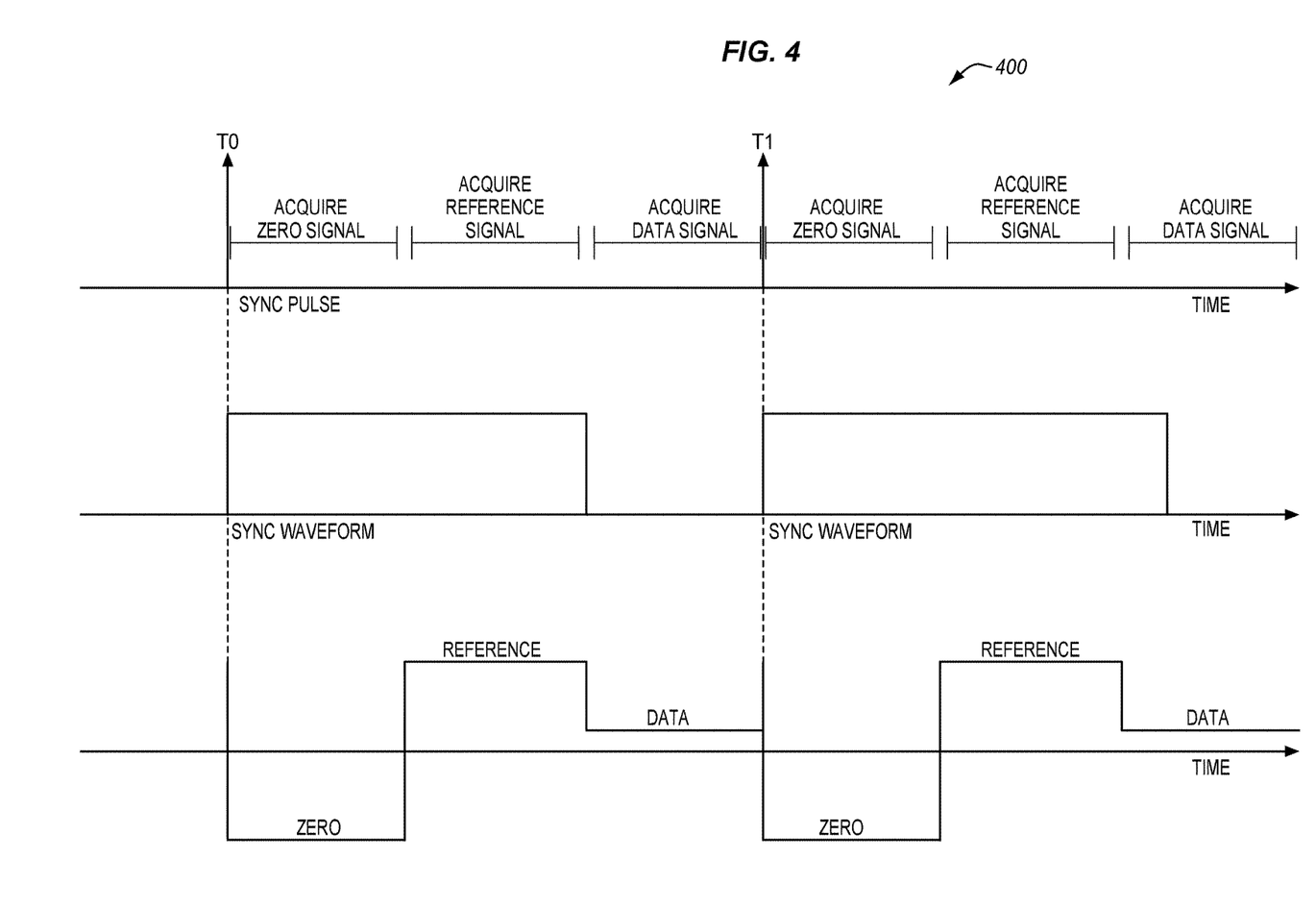
FIG. 4 is a diagram illustrating timing of signal acquisition for the system of FIG. 1 in an exemplary embodiment.

FIG. 4 is a diagram 400 illustrating timing of signal acquisition for system 100 of FIG. 1 in an exemplary embodiment. Specifically, FIG. 4 illustrates multiple waveforms (starting at time T0 and T1, respectively) that each include a period in which a zero state is measured, a period in which a reference state is measured, and a period in which a sample state is measured. A sync waveform is also illustrated, which may be provided by sensor 118 in order to synchronize acquisition of zero values, reference values, and sample values at detector 146.

Figure 5:
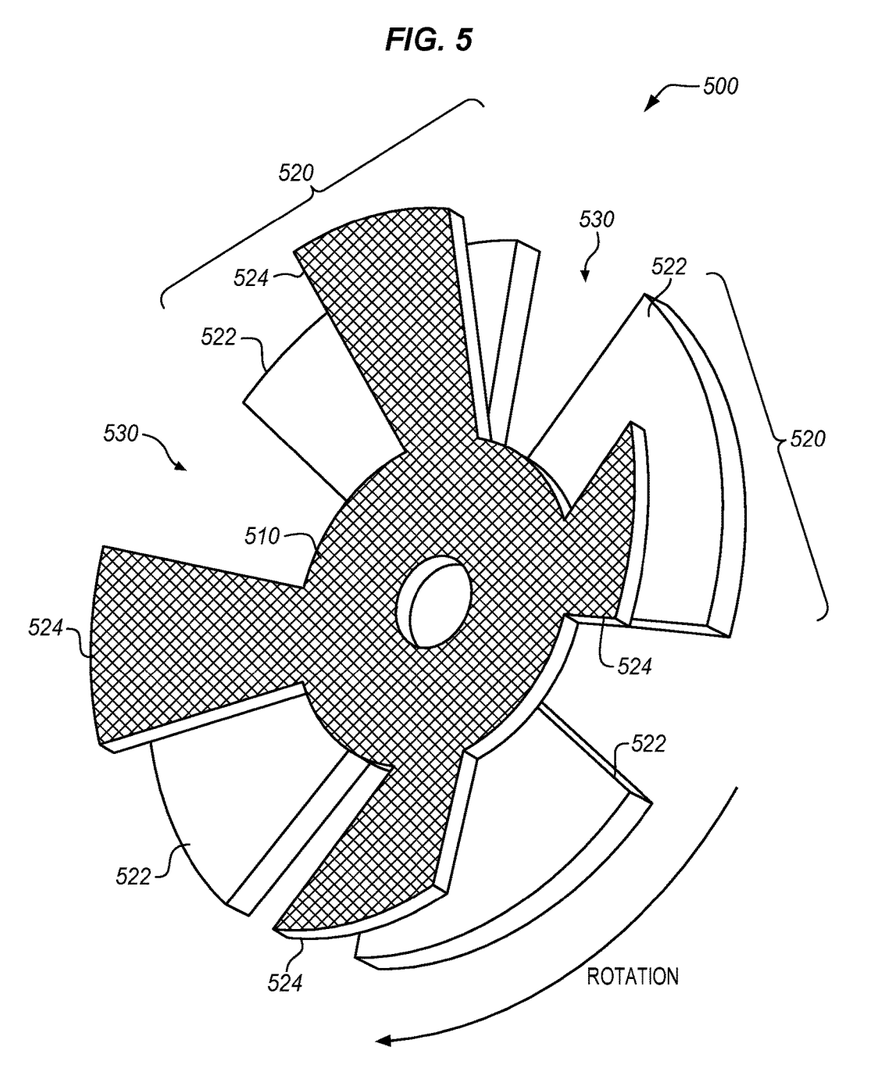
FIGS. 5-7 are views of a chopper that performs TDM for a laser in an exemplary embodiment.
Figure 6:
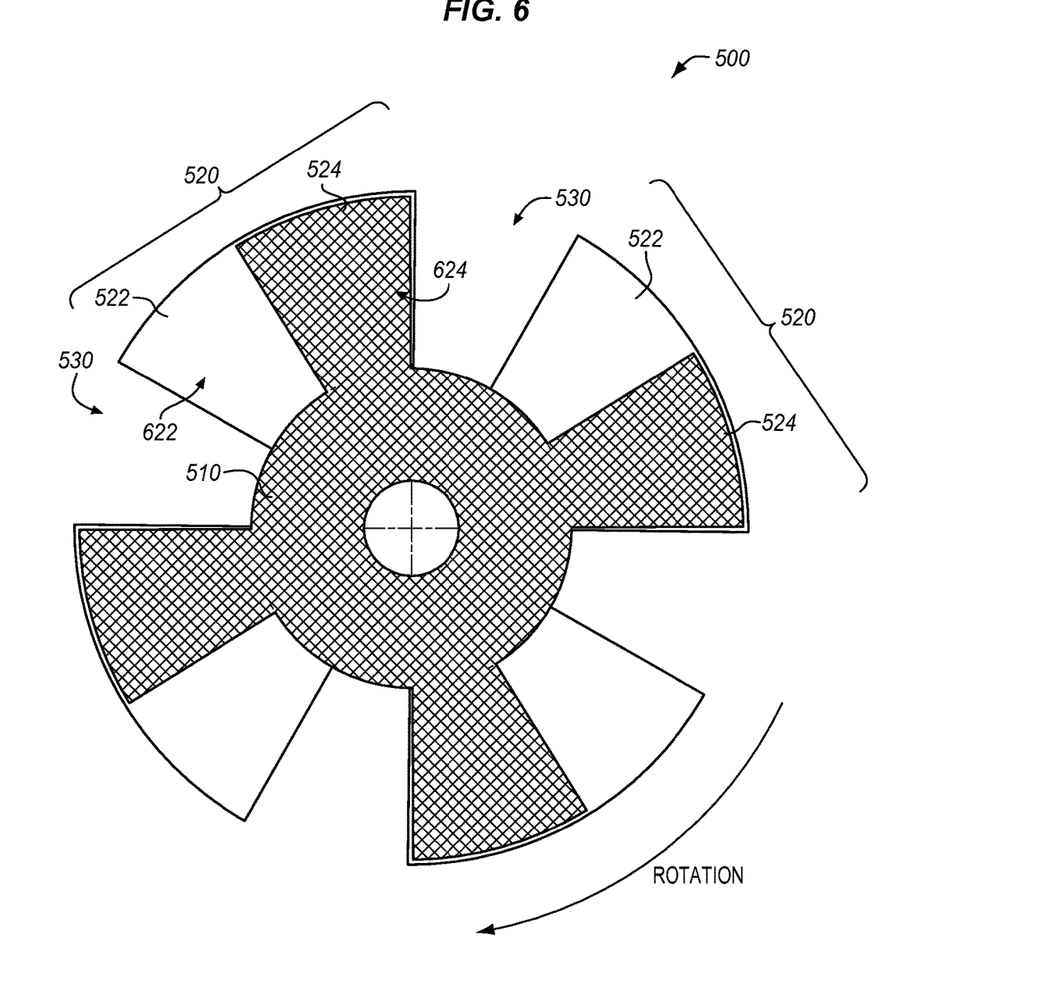
Figure 7:
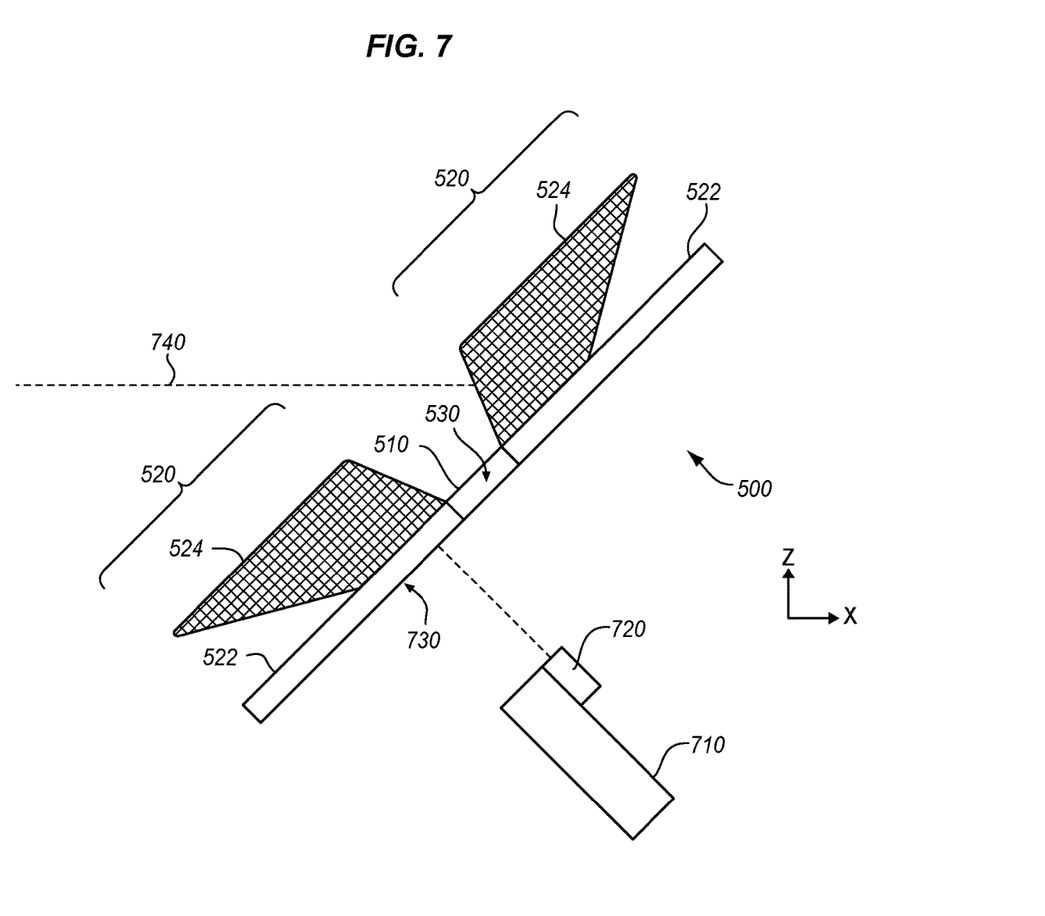

With a description of the operations of system 100 provided above, FIGS. 5-7 illustrate an exemplary embodiment of an optical chopper 500 that performs TDM in an exemplary embodiment. FIG. 5 is a perspective view of optical chopper 500, and illustrates that chopper 500 includes base 510, from which multiple sets 520 of fins extend. Each set 520 of fins is located along a different arcuate portion of chopper 500. The fins include a reflective fin 522 that redirects a beam of light along the reference path, and a light blocking fin 524 (e.g., a non-reflective matte black fin) that prevents the beam from entering sphere 140. Chopper 500 further defines gaps 530 (e.g., notches or grooves). The beam may travel directly through gaps 530 to arrive at sample 150. Chopper 500 includes four sets 520 of fins, and spins at a rate between fifteen times per second and twenty-five times per second. This cycles between iterations of the sample state, zero state, and reference state at a rate of 60-100 Hz. That is, while chopper 500 is at a first angle of rotation it may block the beam, while chopper 500 is at a second angle of rotation it may redirect the beam, and while chopper 500 is at a third angle of rotation it may allow the beam to pass.

FIG. 6 is a face view of chopper 500 illustrating fins 522 and 524, as well as gaps 530. Interactions between chopper 500 and a beam from laser 110 are illustrated with regard to FIG. 7. As shown in FIG. 7, base 510 of chopper 500 is angled upward from the X axis (e.g., rotated along the Y axis by forty five degrees). This causes beam 740 to strike surface 624 of blocking fins 524 orthogonally, ensuring that beam 740 is fully blocked. The orientation of chopper 500 further facilitates redirection of beam 740 by reflective surface 622 of reflective fins 522. A light emitting sensor 710 (i.e., an embodiment of sensor 118) measures the rotation of chopper 500 by emitting light from light source 720. When the emitted light is reflected by reflective fins 522, a large amount of reflectance is detected, and the sync waveform is generated as shown in FIG. 4. When gaps 530 rotate past sensor 710, light is not reflected back to sensor 710, and hence a space between sync waveforms is detected by controller 130.

In some embodiments, system 100 may be calibrated based on the introduction of a "sample" having known reflectance properties, such as a sample of reflective copper. The measurements acquired for this sample may be utilized by controller 130 to calculate the correction factors mentioned above. For example, a correction factor for each angle of incidence may be calculated based on Fresnel equations as described in M. Born and E. Wolf, "Principles of Optics", Sixth Edition (Pergamon, 1980), p. 40. Once these correction factors have been determined, they may be utilized over and again (e.g., for many or all samples measured in system 100).

Any of the various control elements (e.g., electrical or electronic components) shown in the figures or described herein may be implemented as hardware, a processor implementing software, a processor implementing firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, a control element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

What is claimed is:

1. A system comprising:
a laser that emits a beam of light;
an optical chopper disposed between the laser and a sample, the chopper blocks the beam while the chopper is at a first angle of rotation, redirects the beam along a reference path while the chopper is at a second angle of rotation, and permits the beam to follow a sample path through the chopper and strike the sample while the chopper is at a third angle of rotation; and
a hollow sphere that defines a slot through which the sample path and reference path enter the sphere, the hollow sphere comprising:
a spectral hemispherical reflectance detector;
a mount that receives the sample at the sphere;
an inner surface of the hollow sphere that receives the beam when the beam is redirected along the reference path; and
an actuator that rotates the sphere about an axis of rotation that intersects the sample.

2. The system of claim 1 further comprising:
a light source that emits light onto the chopper;
a reflective sensor that measures light from the light source that has been reflected by the chopper; and
a controller that determines when the beam is following the reference path, is following the sample path, and is blocked based on input from the reflective sensor, and that calculates a spectral hemispherical reflectance of the sample based on input from the detector when the beam is following the reference path, when the beam is following the sample path, and when the beam is blocked.

3. The system of claim 1 wherein:
rotation of the sphere about the axis of rotation alters an angle of incidence of the sample path to the sample, and
the sphere is rotatable about the axis of rotation to provide a range of angles of incidence between the sample path and the sample from zero degrees to at least eighty seven degrees.

4. The system of claim 1 wherein:
the optical chopper comprises a rotatable wheel that includes sets of fins that each occupy a different arcuate portion of the wheel, each set of fins comprising:
a first fin that blocks the beam while the chopper is at the first angle of rotation; and
a second fin that redirects the beam along a reference path while the chopper is at the second angle of rotation; and
the chopper defines gaps between the sets of fins that permit the beam to follow a sample path through the chopper and strike the sample while the chopper is at the third angle of rotation.

5. The system of claim 4 wherein:
for each set of fins, the first fin is oriented orthogonal to the beam and is non-reflective, and the second fin is reflective.

6. The system of claim 1 further comprising:
a half-wave plate and a polarizer disposed between the laser and the chopper that linearly polarize the beam.

7. The system of claim 1 wherein:
the laser is tunable;
the system further comprises a half-wave plate and a polarizer that linearly polarize the beam; and
the system further comprises a controller that automatically adjusts wavelength of the beam via the tunable laser, adjusts polarization of the beam via the half-wave plate and the polarizer, and directs the actuator to alter an angle of incidence of the beam with the sample by rotating the sphere.

8. A method comprising:
emitting a beam of light from a laser;
time domain multiplexing the beam, thereby causing the beam to iteratively:
follow a sample path that proceeds through a slot at a hollow sphere to strike a sample at the sphere;
follow a reference path that proceeds through the slot to strike an interior surface of the sphere; and
be blocked;
acquiring, via a detector within the sphere, measurements of spectral hemispherical reflectance while the beam is being time domain multiplexed;
correlating the measurements with time periods when the beam followed the sample path, followed the reference path, and was blocked;
calculating a spectral hemispherical reflectance of the sample based on the correlated measurements; and
updating a memory with the calculated spectral hemispherical reflectance of the sample.

9. The method of claim 8 further comprising:
rotating the sphere about an axis of rotation that intersects the sample, thereby altering an angle of incidence at which the sample path intersects the sample.

10. The method of claim 9 further comprising:
iteratively performing the time domain multiplexing, the acquiring, the correlating, the calculating, and the rotating such that spectral hemispherical reflectance of the sample is determined across a range of angles of incidence between zero degrees and at least eighty seven degrees.

11. The method of claim 9 further comprising:
adjusting a polarization of the beam; and
repeating the method.

12. The method of claim 9 further comprising:
adjusting a wavelength of the beam; and
repeating the method.

13. The method of claim 8 wherein:
time domain multiplexing the beam comprises rotating a chopper disposed between the laser and a sample, the chopper comprising a rotatable wheel that includes fins and gaps that each occupy a different arcuate portion of the wheel.

14. The method of claim 8 further comprising:
emitting light from a light source onto a chopper that performs the time domain multiplexing; and
determining the time periods based on input from a sensor measuring reflection of the emitted light.

15. A non-transitory computer readable medium embodying programmed instructions which, when executed by a processor, are operable for performing a method comprising:
emitting a beam of light from a laser;
time domain multiplexing the beam, thereby causing the beam to iteratively:
follow a sample path that proceeds through a slot at a hollow sphere to strike a sample at the sphere;
follow a reference path that proceeds through the slot to strike an interior surface of the sphere; and
be blocked;
acquiring, via a detector within the sphere, measurements of spectral hemispherical reflectance while the beam is being time domain multiplexed;
correlating the measurements with time periods when the beam followed the sample path, followed the reference path, and was blocked;
calculating a spectral hemispherical reflectance of the sample based on the correlated measurements; and
updating a memory with the calculated spectral hemispherical reflectance of the sample.

16. The medium of claim 15 wherein the method further comprises:
rotating the sphere about an off-center axis of rotation that intersects the sample, thereby altering an angle of incidence at which the sample path intersects the sample.

17. The medium of claim 16 wherein the method further comprises:
iteratively performing the time domain multiplexing, the acquiring, the correlating, the calculating, and the rotating such that spectral hemispherical reflectance of the sample is determined across a range of angles of incidence between zero degrees and at least eighty seven degrees.

18. The medium of claim 15 wherein the method further comprises:
adjusting a polarization of the beam; and
repeating the method.

19. The medium of claim 15 wherein the method further comprises:
adjusting a wavelength of the beam; and
repeating the method.

20. The medium of claim 15 wherein:
time domain multiplexing the beam comprises rotating a chopper disposed between the laser and a sample, the chopper comprising a rotatable wheel that includes fins and gaps that each occupy a different arcuate portion of the wheel.

* * * * *